(12) United States Patent
Trollsas et al.

(10) Patent No.: US 9,205,456 B2
(45) Date of Patent: Dec. 8, 2015

(54) MODIFYING POLYMER PROPERTIES WITH PENETRANTS IN THE FABRICATION OF BIORESORBABLE SCAFFOLDS

(75) Inventors: Mikael Trollsas, San Jose, CA (US); John Stankus, Campbell, CA (US); Michael H. Ngo, San Jose, CA (US); Wen Chung Tsai, Hagersten (SE); Thierry Glauser, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/556,986

(22) Filed: Jul. 24, 2012

(65) Prior Publication Data
US 2014/0030422 A1  Jan. 30, 2014

(51) Int. Cl.
*B05D 5/00* (2006.01)
*A61L 31/06* (2006.01)
*A61L 31/14* (2006.01)

(52) U.S. Cl.
CPC . *B05D 5/00* (2013.01); *A61L 31/06* (2013.01); *A61L 31/141* (2013.01)

(58) Field of Classification Search
CPC .......................................................... B05D 5/00
USPC ...................................... 623/1.15, 1.34, 1.38
See application file for complete search history.

(56) References Cited

U.S. PATENT DOCUMENTS

| | | | |
|---|---|---|---|
| 8,043,553 B1 | 10/2011 | Durcan | |
| 8,173,062 B1 | 5/2012 | Durcan | |
| 2003/0083732 A1* | 5/2003 | Stinson | 623/1.15 |
| 2007/0283552 A1 | 12/2007 | Gale et al. | |
| 2008/0275537 A1 | 11/2008 | Limon | |
| 2009/0149940 A1* | 6/2009 | Wang et al. | 623/1.15 |
| 2009/0319028 A1 | 12/2009 | Ramzipoor et al. | |
| 2010/0004735 A1 | 1/2010 | Yang et al. | |
| 2010/0262224 A1 | 10/2010 | Kleiner | |
| 2011/0021717 A1 | 1/2011 | Wang et al. | |
| 2011/0190871 A1 | 8/2011 | Trollsas et al. | |
| 2011/0190872 A1 | 8/2011 | Anukhin et al. | |

FOREIGN PATENT DOCUMENTS

WO   WO 2007/164410   12/2007

OTHER PUBLICATIONS

Naebe et al, Electrospun single-walled carbon nantube/polyvinyl alcohol composite nanofibers:structure-property relationships, 2008, Nanotechnology, No. 19, pp. 1-8.*
McNally et al., Antec'97 Plastics Saving Planet Earth Conference Proveedings, Apr. 1997, Society of PLastics Engineers, vol. 3., pp. 1-8.*
U.S. Appl. No. 13/549,366, filed Jul. 13, 2012, Eli et al.
Cairncross et al., "Moisture Sorption and Transport in Polylactide", Int. Polymer Processing 22 (1), pp. 33-37 (2007).

(Continued)

*Primary Examiner* — Dah-Wei D Yuan
*Assistant Examiner* — Andrew Bowman
(74) *Attorney, Agent, or Firm* — Squire Patton Boggs (US) LLP

(57) ABSTRACT

Methods of fabricating a bioresorbable polymer scaffold are disclosed including a step of inducing crystallization in a bioresorbable polymer construct through exposure to a liquid penetrant.

2 Claims, 18 Drawing Sheets

(56) References Cited

OTHER PUBLICATIONS

Shibata et al., "Mechanical properties, morphologies, and crystallization behavior of plasticized poly(L-lactide)/poly(butylene succinate-*co-L-lactate*) blends", Polymer 48 (9), pp. 2768-2777 (2007).

Tool et al., "Variations caused in the heating curves of glass by heat treatment", J. of Am. Ceramic Soc. vol. 14, 35 pgs (1931).
Van Vlack "Elements of Materials Science and Engineering", Book, $6^{th}$ Ed. pp. 270-271 (1989).
International Search Report for PCT/US2013/034679, mailed Jul. 3, 2013, 4 pgs.

* cited by examiner

MODIFYING POLYMER PROPERTIES WITH PENETRANTS IN THE FABRICATION OF BIORESORBABLE SCAFFOLDS

BACKGROUND OF THE INVENTION

1. Field of the Invention

This invention relates polymeric medical devices, in particular, bioresorbable stents or stent scaffoldings.

2. Description of the State of the Art

This invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. A medicated stent may be fabricated by coating the surface of either a metallic or polymeric scaffold with a polymeric carrier that includes an active or bioactive agent or drug. Polymeric scaffolds may also serve as a carrier of an active agent or drug. An active agent or drug may also be included on a scaffold without being incorporated into a polymeric carrier.

The stent must be able to satisfy a number of mechanical requirements. The stent must be capable of withstanding the structural loads, namely radial compressive forces, imposed on the scaffold as it supports the walls of a vessel. Therefore, a stent must possess adequate radial strength. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation. Radial strength is measured either by applying a compressive load to a stent between flat plates or by applying an inwardly-directed radial load to the stent.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from materials that erodes or disintegrate through exposure to conditions within the body. Stents fabricated from biodegradable, bioabsorbable, bioresorbable, and/or bioerodable materials such as bioabsorbable polymers can be designed to completely erode only after the clinical need for them has ended.

A drawback of bioresorbable polymers as compared to metals used for stent is that polymers typically have lower strength. Therefore, an important aspect in fabricating bioresorbable polymer scaffolds is processing methods that increase the strength of the polymer.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Embodiments of the present invention include a method of fabricating a bioresorbable stent scaffold comprising: providing tube made of a bioresorbable polymer; exposing the tube to a solvent for a period of time, wherein the solvent is absorbed into the bioresorbable polymer which increases a crystallinity of the bioresorbable polymer; and fabricating a scaffold having a pattern of interconnected struts from the exposed tube.

Embodiments of the present invention include a method of fabricating a bioresorbable stent scaffold comprising: providing tube made of a bioresorbable polymer; exposing the tube to a fluid comprising methanol for a period of time, wherein the fluid is absorbed into the bioresorbable polymer which increases a crystallinity of the bioresorbable polymer; and fabricating a scaffold having a pattern of interconnected struts from the exposed tube.

Embodiments of the present invention include a method of fabricating a bioresorbable stent scaffold comprising: providing tube made of a bioresorbable polymer; exposing the tube to a fluid comprising methanol for a period of time, wherein the solvent is absorbed into the bioresorbable polymer and increases a flexibility of the bioresorbable polymer; radially expanding the exposed tube comprising the absorbed fluid from a first diameter to a second diameter; and fabricating a scaffold having a pattern of interconnected struts from the radially expanded tube.

Embodiments of the present invention include a method comprising: providing a scaffold made of a bioresorbable polymer comprising absorbed penetrant that decreases a modulus and increases an elongation at break of the bioresorbable polymer, wherein the penetrant is a fluid comprising methanol or ethanol; and crimping the scaffold from a first diameter to a reduced diameter over a delivery balloon.

DETAILED DESCRIPTION OF THE INVENTION

The methods described herein are generally applicable to any amorphous or semi-crystalline polymeric implantable medical device, especially those that have load bearing portions when in use or have portions that undergo deformation during use. In particular, the methods can be applied to tubular implantable medical devices such as self-expandable stents, balloon-expandable stents, and stent-grafts.

Figure 1:
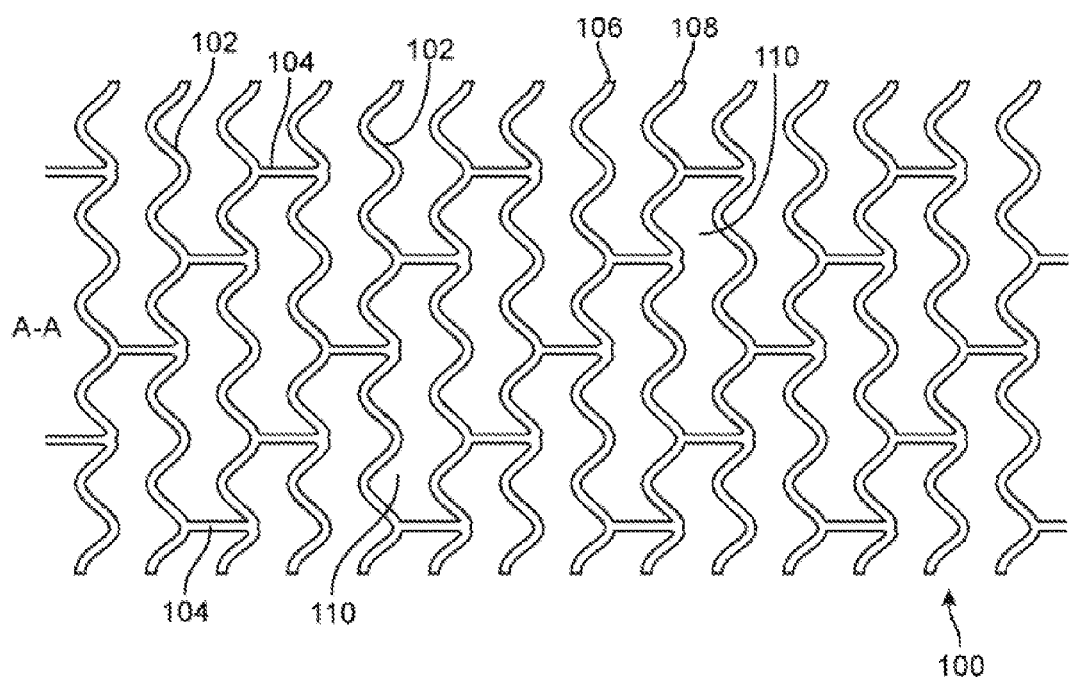
FIG. 1 depicts a stent.

FIG. 1 illustrates a portion of an exemplary stent or scaffold pattern 100. The pattern 100 of FIG. 1 represents a tubular scaffold structure so that an axis A-A is parallel to the central or longitudinal axis of the scaffold. FIG. 1 shows the scaffold in a state prior to crimping or after deployment. Pattern 100 is composed of a plurality of ring struts 102 and link struts 104. The ring struts 102 forms a plurality of cylindrical rings, for example, rings 106 and 108, arranged about the cylindrical axis A-A. The rings are connected by the link struts 104. The scaffold comprises an open framework of struts and links that define a generally tubular body with gaps 110 in the body defined by rings and struts. The cylindrical tube of FIG. 1 may be formed into this open framework of struts and links described by a laser cutting device that cuts such a pattern into a thin-walled tube that may initially have no gaps in the tube wall.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

A stent or scaffold of the present invention can be made partially or completely from a biodegradable, bioresorbable, and bioabsorbable polymer. The stent can also be made in part of a biostable polymer. A polymer for use in fabricating stent can be biostable, bioresorbable, bioabsorbable, biodegradable or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

Exemplary embodiments of stent patterns for coronary and other applications is described in U.S. application Ser. No. 12/447,758 (US 2010/0004735) to Yang & Jow, et al. Other examples of suitable stent patterns are found in US 2008/0275537. The thickness of the scaffold may be between 130 and 180 microns. An exemplary cross-section of the struts of a scaffold is 150×150 microns. The scaffolds may have a pre-crimping or an as-fabricated diameter of between 2.5 to 4 mm, more narrowly, 3 to 3.5 mm, or at or about 2.5 mm, 3 mm, or 3.5 mm. The scaffold can be crimped from the as-fabricated diameter over a semi-compliant or non-compliant balloon to a crimped profile of about a 1.8 to 2.2 mm diameter (e.g., 2 mm). The scaffold may be deployed to a diameter of between about 3 mm and 4 mm.

Exemplary stent scaffold patterns for the superficial femoral artery (SFA) and other applications are disclosed in US2011/0190872, US2011/0190871, and U.S. patent application Ser. No. 13/549,366. As compared to coronary stents, a peripheral (SFA) stent scaffold usually has lengths of between about 36 and 60 mm or even between 40 and 200 mm when implanted in the superficial femoral artery, as an example. The scaffold for SFA may have a pre-crimping diameter of between 5-10 mm, or more narrowly 6-8 mm, and can possess a desired pinching stiffness while retaining at least a 80% recoverability from a 50% crush. The scaffold for SFA may have a wall thickness of about 0.008" to 0.014" and configured for being deployed by a non-compliant balloon, e.g., 6.5 mm diameter, from about a 1.8 to 2.2 mm diameter (e.g., 2 mm) crimped profile. The SFA scaffold may be deployed to a diameter of between about 4 mm and 7 mm.

Such scaffolds may further include a polymer coating which optionally includes a drug. The coating may be conformal (around the perimeter of the scaffold) and may be 2-8 microns thick. In other embodiments described herein, the scaffolds may be made partly out of the composite.

Bioresorbable stents can be useful for treatment of various types of bodily lumens including the coronary artery, superficial femoral artery, popliteal artery, neural vessels, and the sinuses. In general, these treatments require the stent to provide mechanical support to the vessel for a period of time and then desirably to absorb away and disappear from the implant site. The important properties of a bioabsorbable stent or scaffolding include mechanical and degradation properties. The mechanical requirements include high radial strength, high radial stiffness, and high fracture toughness. The degradation properties include the absorption profile, for example, the change in molecular weight, radial strength, and mass with time.

With respect to radial strength and stiffness, a stent should have sufficient radial strength and/or stiffness to withstand structural loads, namely radial compressive forces, imposed on the stent so that the stent can support the walls of a vessel at a selected diameter for a desired time period. A polymeric stent with adequate radial strength and/or stiffness enables the stent to maintain a lumen at a desired diameter for a sufficient period of time after implantation into a vessel.

In addition, the stent should possess sufficient toughness or resistance to fracture to allow for crimping, expansion, and cyclic loading without fracture or cracking that would compromise the function of the stent. The toughness or resistance to fracture can be characterized for a material by the elongation at break and for a scaffold by the number and degree of cracks in a scaffold during use, such as after crimping or deployment. These aspects of the use of the stent involve deformation of various hinge portions of the structural elements of the scaffold.

Some bioresorbable polymers, for example, semi-crystalline polymers, are stiff or rigid under physiological conditions within a human body and have been shown to be promising for use as a scaffold material. Specifically, polymers that have a glass transition temperature (Tg) sufficiently above human body temperature which is approximately 37° C., should be stiff or rigid upon implantation. Poly(L-lactide) (PLLA) is attractive as a stent material due to its relatively high strength and a rigidity at human body temperature, about 37° C. As shown in Table 1, PLLA has high strength and tensile modulus compared to other biodegradable polymers. Since it has a glass transition temperature well above human body temperature, it remains stiff and rigid at human body temperature. This property facilitates the ability of a PLLA stent scaffolding to maintain a lumen at or near a deployed diameter without significant recoil (e.g., less than 10%).

Other rigid bioresorbable polymers include poly(D-lactide) (PDLA), polyglycolide (PGA), and poly(L-lactide-co-glycolide) (PLGA). The PLGA include those having a mole % of (LA:GA) of 85:15 (or a range of 82:18 to 88:12), 95:5 (or a range of 93:7 to 97:3), or commercially available PLGA products identified being 85:15 or 95:5 PLGA. Rigid polymers may refer to polymers that have a Tg higher than human body temperature or within 5 deg C. of human body temperature.

TABLE 1

Comparison of properties of bioressorbable polymers.

| | Tm (° C.) | Tg (° C.) | Tensile Strength (MPa) | Tensile Modulus (MPa) | Elongation at break (%) | Absorption Rate |
|---|---|---|---|---|---|---|
| PLLA | 175 | 65 | 28-50 | 1200-2700 | 6 | 1.5-5 years |
| P4HB | 60 | −51 | 50 | 70 | 1000 | 8-52 weeks |
| PCL | 57 | −62 | 16 | 400 | 80 | 2 years |
| PDO | 110[1] | −10[1] | 1.5[1,2] | 30[2] | 35[3] | 6-12[1] 6[2] |
| PGA | 225 | 35 | 70 | 6900 | <3 | 6 weeks |
| DL-PLA | Amorphous | 50-53 | 16 | 400 | 80 | 2 years |
| P3HB | 180 | 1 | 36 | 2500 | 3 | 2 years |

PLLA (poly(L-lactide);
P4HB (poly-4-hyroxybutyrate);
PCL (polycaprolactone);
PGA (polyglycolide);
DL-PLA (poly(DL-lactide);
P3HB (poly-3-hydroxybutyrate);
PDO (p-polydioxanone)
All except PDO, Martin et al., Biochemical Engineering 16 (2003) 97-105.
[1]Medical Plastics and Biomaterials Magazine, March 1998.
[2]Medical Device Manufacturing & Technology 2005.
[3]The Biomedical Engineering Handbook, Joseph D. Bronzino, Ed. CRC Press in Cooperation with IEEE Press, Boca Raton, FL, 1995.

The mechanical properties such as strength and stiffness of a semi-crystalline polymer are highly dependent on and vary with the degree of crystallinity. As a consequence, the radial strength and stiffness of scaffold made from a bioresorbable semi-crystalline polymer is likewise dependent on the crystallinity. In general, the strength and stiffness (and radial strength and radial stiffness) increase with an increase in crystallinity.

The crystallinity of a semi-crystalline polymer construct varies significantly with different processing methods used in its manufacture, where extrusion, injection molding, thermoforming and fiber spinning are among the methods utilized for processing semi-crystalline polymers. The key to altering the mechanical properties is by fine tuning the degree of crystallinity, and the crystal structure to obtain the most desirable properties, which may include fracture toughness, flexibility and mechanical strength, which results in desirable scaffold properties, i.e., reduced scaffold fracture and high radial strength.

The fabrication process of a bioresorbable scaffold can include the following steps:

(1) forming a polymeric tube using extrusion or injection molding, (2) processing step to increase strength of the formed tube, (3) forming a stent scaffolding from the processed tube by laser machining a stent pattern in the tube from step (1) or (2) with laser cutting, (4) optionally forming a therapeutic coating over the scaffolding, (5) crimping the stent over a delivery balloon, and (6) sterilization with election-beam (E-Beam) radiation.

The polymer tube may have walls that are free of any gaps or holes. Detailed discussion of the manufacturing process of a bioabsorbable stent can be found elsewhere, e.g., U.S. Patent Publication No. 20070283552, which is incorporated by reference herein.

In an extrusion step, a polymer is processed in an extruder above the melting temperature of the polymer and then conveyed through a die to form a polymer tube. In step (2) above, the extruded tube may be subjected to a process that modifies the crystallinity of the extruded tube to increase the radial strength of the tube, and thus, the finished scaffold. The increase in strength reduces the thickness of the struts required to support a lumen with the scaffold when expanded at an implant site. In exemplary embodiments, the strut thickness can be 100-250 microns, or more narrowly, 120-180, 130-170, or 140-160 microns, 160 to 200 microns, or 180 to 220 microns.

Previously disclosed processing methods to increase strength include processing methods that modify crystallinity, crystal structure, and morphology. These methods include annealing the polymer tube, typically at a temperature between Tg and Tm of the polymer. A scaffold may then be formed from the annealed polymer tube.

Other methods of increasing strength include radially expanding the tube from an original to an expanded diameter, also typically at a temperature between Tg and Tm. Although crystallinity may be induced due to the temperature, the crystallinity in this method is induced primarily through strain-induced crystallization. A scaffold may then be formed from the tube at the expanded diameter.

Embodiments of the present invention include a scaffold fabrication process that includes a step of exposing a polymer construct to a liquid for a period of time that modifies the crystallinity of the bioresorbable polymer which increases its strength. The liquid penetrates or is absorbed into the bioresorbable polymer and induces or increases the crystallinity of the bioresorbable polymer. The polymer construct is an intermediate in a scaffold fabrication process, for example, a polymer tube.

The method can include obtaining or making a polymer tube and exposing the polymer tube to a liquid penetrant for a period of time. The crystallinity of the polymer tube is induced or increased during this exposure. A scaffold may be the fabricated from the exposed tube through laser machining a pattern into the tube. A bioresorbable scaffold is fabricated scaffold from the exposed tube. The resulting scaffold has increased strength due to the increased crystallinity. Some or all of the penetrant can be removed from the exposed tube prior to fabricating the scaffold.

The exposure to the penetrant can be performed at ambient temperature which is at or about 25 deg C., or 20 to 30 deg C. Additionally, the exposure can be performed at a temperature greater than ambient, for example, at or about 37 deg C. or 37 to 45 deg C. Exposure at a particular temperature can be achieved by exposing a sample to a penetrant that is at a particular temperature.

In some embodiments, the exposed polymer tube is radially expanded to an expanded diameter and a scaffold can be fabricated from the tube at the expanded diameter. The tube can be radially expanded prior to removal of the penetrant from the tube. In this case, the penetrant may plasticize the polymer enabling radial expansion at a temperature below the dry Tg of the polymer. For example, the tube may be expanded at about ambient temperature, 25 deg C., or 20 to 30 deg C. Alternatively, some or all of the penetrant can be removed from the polymer tube prior to the radial expansion. In this case where all the penetrant is removed, the tube may be expanded at a temperature between Tg and Tm of the dried exposed tube.

In other embodiments, a scaffold is fabricated from the exposed tube with no radial expansion of the exposed tube.

The liquid or penetrant is defined as a fluid that is capable of penetrating or being absorbed into a polymer into the bulk of the polymer and further capable of modifying crystallinity of the polymer upon the penetration or absorption. The penetrant may penetrate the polymer through one or more molecular diffusion mechanisms. For example, the diffusion of penetrants in the polymer can be Fickian (case I) or non-Fickian The penetrant is further capable of penetrating or the swelling the polymer without dissolving the polymer.

The induced crystallization may be referred to as solvent-induced crystallization. Solvent-induced crystallization is a complex phenomenon involving the coupled processes of diffusion, swelling, and crystallization. Several variables can affect the rate and/or extent of each process and the development of crystalline morphology including initial crystallinity/orientation, molecular weight distribution, and solvent chemistry. Without being limited by theory, a solvent or penetrant diffuses into a polymer and induces crystallization because the solvent lowers the crystallization temperature of the polymer. In particular, absorption of a penetrant by the polymer tends to decrease the Tg of the polymer. As a result of a decrease of the Tg, the temperature at which polymer chains may have sufficient mobility to align and crystallize decrease.

Suitable penetrants depend on the type of polymer and its crystalline morphology since different penetrants will have a different effect on the given polymer. Representative penetrants for PLLA and other polymers include, but are not limited to, methanol, ethanol, isopropyl alcohol, acetone, and chloroform.

Representative methods of exposing the tube can include, but are not limited to, immersing and soaking the tube in the penetrant, spraying the tube with the penetrant, and applying the penetrant with an applicator such as a brush.

The polymer tube is exposed a polymer for a period of time which can be 1 to 4 hr, 4 hr to 24 hr or 1 day, 1 to 4 days, 4 days to 1 week, and 1 week to 4 weeks. The time of exposure can be determined or dictated by crystallinity modification and/or mechanical property modification provided by a given penetrant in a given time frame. The amount of penetrant absorbed (% uptake of penetrant), the kinetics or rate of uptake of penetrant, and the magnitude and time for saturation of the polymer depend on the given penetrant-polymer combination.

In general, it is desired to achieve particular crystallinity modification and mechanical property modification in the shortest time. This makes a manufacturing process more efficient.

The mechanical properties of the bioresorbable polymer can be modified by the exposure to the penetrant, while still absorbed in the polymer. The modulus of a soaked material may decrease by 10 to 20%, 20 to 30%, 30 to 40%, by at least 30%, or by at least 40%. Depending on the penetrant and polymer combination, the drip can occur in 1 to 2 hr, 2 to 24 hr, 1 to 8 days, 6 to 8 days, or 8 to 10 days. The elongation at break of a soaked material may increase by 40 to 50%, 50 to 70%, 70 to 100%, 100 to 150%, 150 to 200%, 200 to 250%, by at least 100%, or by at least 200%. Depending on the penetrant and polymer combination, the increase can occur in 1 to 2 hr, 2 to 24 hr, 1 to 8 days, 6 to 8 days, or 8 to 10 days.

The inventors have found for PLLA surprising and unexpected differences among solvents in the % uptake, kinetics of the uptake, saturation uptake, effect on mechanical properties in the dry and wet states, penetration mechanisms, effect glass transition properties, and degree of crystallinity induced.

The % uptake of penetrant in the tube is defined as:

$$\frac{\text{exposed sample weight} - \text{initial sample weight}}{\text{initial sample weight}}$$

where a sample can be a polymer tube. The % uptake of penetrant of can be 1 to 6%, 1 to 10%, 1 to 2%, 1 to 4%, 2 to 4%, or 2 to 6%. The polymer sample may be exposed for the period of time to reach a saturation % uptake, which is the maximum % uptake for a particular polymer sample. The polymer may also be exposed for a period of time to reach a % uptake that is below a saturation level.

The initial crystallinity of tube can be amorphous or substantially amorphous. For example, the initial crystallinity can be less than 5%; less than 1%, less than 2%, or less than 5%. The initial crystallinity can also be 1 to 5%, 1 to 2%, or 2 to 5%. The tube can also be semi-crystalline prior to exposure and have an initial crystallinity of 10 to 55%, 10 to 20%, 20 to 30%, 30 to 40%, or 40 to 55%. The semi-crystalline tube can be a polymer tube has been subjected to another type of crystallinity modification process, such as annealing or radial expansion.

In some embodiments, a scaffold including absorbed penetrant is crimped over a delivery balloon from an as-fabricated diameter to a reduced crimped diameter. The concentration of penetrant can be as described above. As shown in Table 4, the absorbed penetrant can decrease the modulus and increase the elongation of break of the bioresorbable polymer of a tube. Therefore, fracture during the crimping process can be reduced or eliminated. The scaffold may be at ambient temperature during crimping. After crimping, the penetrant can be removed from the scaffold through evaporation at ambient temperature or by heating the scaffold to a temperature above ambient temperature, for example, 30 to 45 deg C.

In some embodiments, a scaffold can be made from a tube that includes no penetrant. The scaffold may then be exposed to a penetrant in a manner disclosed above for a tube. The scaffold can then be crimped as described.

EXAMPLES

A study was conducted to investigate the modification of PLLA constructs through exposure to various types of penetrants, in order to alter and tailor the mechanical properties to enhance the product quality in a manufacturing process. The penetrants studied included water, ethanol and methanol.

The following were studied:
penetrant sorption, desorption, and kinetics were studied gravimetrically;
thermal analysis using differential scanning calorimetry (DSC) which was used to study the change in fictive temperature (glassy structure), glass transition temperature, cold crystallization temperature;
crystal structure using wide angle x-ray scattering; and
mechanical testing.

Studies were performed on amorphous and semi-crystalline PLLA samples. The amorphous PLLA samples were extruded tubes with an outer diameter (OD) of 4 mm and a wall thickness of 1.5 mm. The semi-crystalline PLLA samples were expanded extruded tubes with an OD of 9 mm and wall thickness of 200 microns.

Penetrant Sorption, Desorption and Kinetics

Prior to the sorption studies, the materials were dried in vacuum for 2 weeks to obtain completely dried samples in order to make sure that the measured change of weight is due to sorption of penetrant and not moisture from the air. Three different penetrants were used for the sorption studies: water, ethanol and methanol. The sorption was conducted by soaking the samples at 37° C. and measuring the weight change gravimetrically with Precisa high precision balance model XR 205 SM-DR. The uptake was measured in percentage, calculated by dividing the mass increase with the initial mass after drying the samples in vacuum and before the soaking.

Desorption of the samples were conducted in an auto-dessicator from Secador with blue gel dessicant placed inside, furthermore, the box was equipped with a ventilation engine to provide the box with fresh air and keep it free from chemicals, like alcohol in this case.

Three samples were used for each experiment. In addition, the samples were cut and prepared in a way that enables the use of one-dimensional diffusion equation, and for sorption kinetics obeying Fickian diffusion, following expression can be used to calculate the diffusion constant D:

$$D = \frac{0.049 l^2}{t_{1/2}}$$

Thermal Analysis

Thermal analyses were characterized by using differential scanning calorimeter (DSC). The DSC studies were conducted by soaking the PLLA samples for various times in the three different penetrants water, ethanol and methanol. The soaking times were 1, 5, 25, 72 h, 1 week and 4 weeks. The data was obtained and performed with a Mettler Toledo DSC 1 differential scanning calorimeter using Mettler Toledo STARe V9.2 software. This was conducted in order to measure the change of fictive temperature, $T_f$, and change of crystallinity in the samples as a function of soaking and aging time. The samples were characterized in both wet and dry state. In the wet state the DSC was conducted immediately after soaking without removing penetrant, while in the dry state, the samples were dried in vacuum oven 3-20 days, depending on penetrant and soaking time, also with help from desorption curves, to make sure the samples were completely dry.

The amorphous PLLA samples were cut along the axial direction of the tubes, while semi-crystalline PLLA samples were cut in small pieces in order to gain continuous contact with the bottom of the DSC cup to reduce noise. The samples size were about 15 mg per each, and a heating rate of 10 K/min for the amorphous- and semi-crystalline PLLA were used. On both the amorphous and semi-crystalline PLLA samples the DSC cups was sealed and isolated without ventilation holes.

DSC data and thermograms were used to calculate the fictive temperature, $T_f$, (glassy state) of the polymer.

Wide-Angle X-Ray Diffraction (WAXD)

WAXD analysis was performed on an X'Pert PRO PANalytical (Cu Kα radiation) under a voltage of 45 kV and a current of 35 mA. Data evaluation was performed on X'Pert High Score Plus. The 2θ-angle was in an angular range of 2° to 60°. Amorphous and semi-crystalline PLLA samples were analyzed at the end of the soaking experiments.

Tensile Testing

Tensile testing was conducted with an Instron 5944 Universal Testing machine, in order to see the change of mechanical properties as a function of penetrant and soaking time. The Instron was equipped with a 50 N load cell. The samplings were performed with a pulling rate at 100 mm/min, and distances of 10 mm between the grips were used. Due to the tube shaped geometry the samples were not formed as dumbbells; instead they were linearly marked with straight lines approximately 2 mm with ruler followed by cutting them in thin stripes along the axial direction.

Results for Penetrant Sorption, Desorption, and Kinetics

Water Sorption, Desorption and Kinetics

Figure 2:
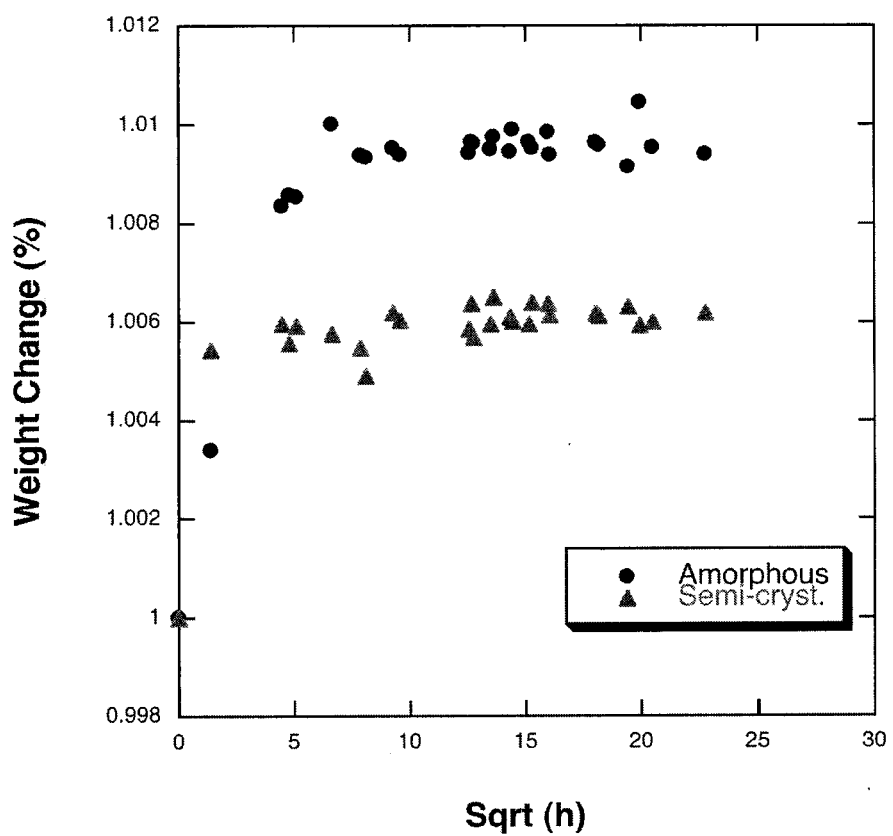
FIG. 2 shows the average sorption uptake value, weight change in %, from the amorphous and semi-crystalline PLLA samples soaked in water.

FIG. 2 shows the water sorption of amorphous PLLA and semi-crystalline PLLA samples soaked in water as a function of the square root of time $(h)^{1/2}$. Both the amorphous and semi-crystalline PLLA obeys Fickian (case I) diffusion behavior. In both cases, the initial part of the curve is linear, and when sorption saturation is reached the curve levels off and a constant mass increase is obtained. The amorphous PLLA samples reached saturation in about 2 days and the water uptakes were approximately 0.1%. The semi-crystalline PLLA samples reached saturation much faster, and were fully saturated within one day. However, the water uptakes were approximately 0.06% and lower for the semi-crystalline samples than the amorphous PLLA samples. The sorption values of amorphous and semi-crystalline PLLA correlates with values obtained by isothermal sorption at 40° C. and 90% relative humidity (RH), R. A. Cairncross, S. Ramaswamy, R. O'Connor: International Polymer Processing (2007), 22, (1), 33-37.

An explanation for the lower water uptake of the semi-crystalline PLLA could be due to the degree of crystallinity in the samples. It is believed that the sorption mechanism is diffusion into the material through the amorphous phase and not through the semi-crystalline phase. If this is the case, this means that when sorption of an amorphous polymer has reached equilibrium, it is the highest sorption possible that this material can reach. However, for a semi-crystalline polymer the highest sorption possible is the same as the amorphous polymer less the degree of crystallinity in the polymer. In the present case the semi-crystalline polymer has a crystallinity of approximately 40%, meaning that the water uptake of the semi-crystalline PLLA samples can reach 60% water sorption of the amorphous PLLA samples.

Figure 3:
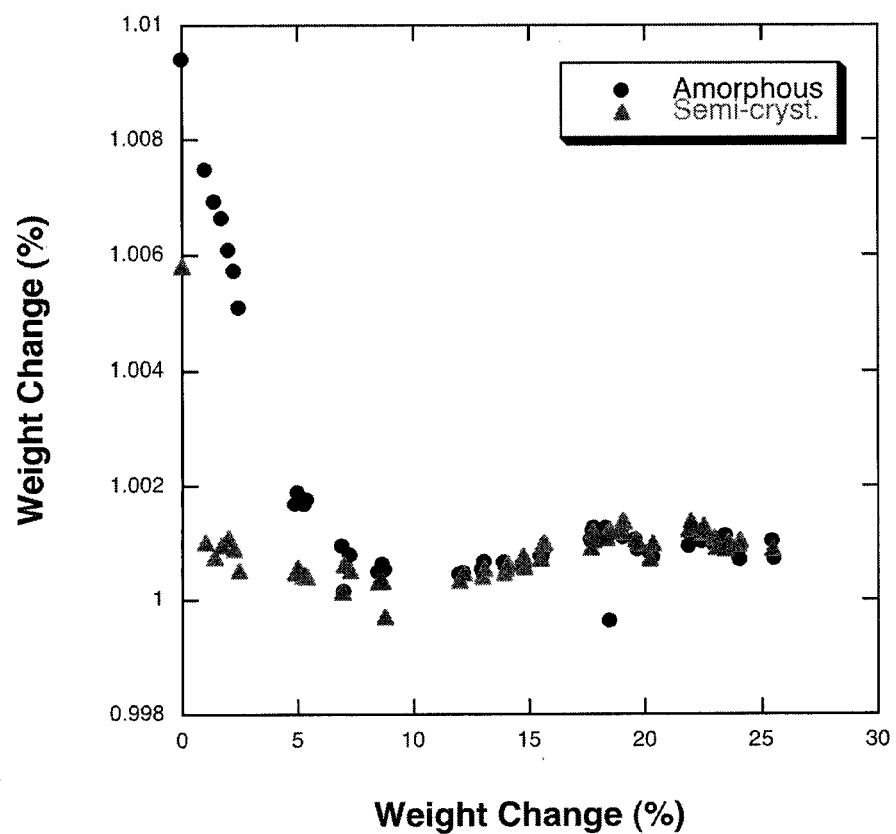
FIG. 3 shows the average desorption value, weight change in %, from the amorphous and semi-crystalline PLLA samples soaked in water.

FIG. 3 shows the desorption curves of the water soaked PLLA samples. Desorption kinetics of the samples correlates to the sorption kinetics of the amorphous and semi-crystalline PLLA samples, meaning that fast sorption also results in fast desorption as in the case of semi-crystalline PLLA samples, whereas the amorphous PLLA samples that showed a slower uptake also showed a slower desorption.

Methanol Sorption and Kinetics

Figure 4:
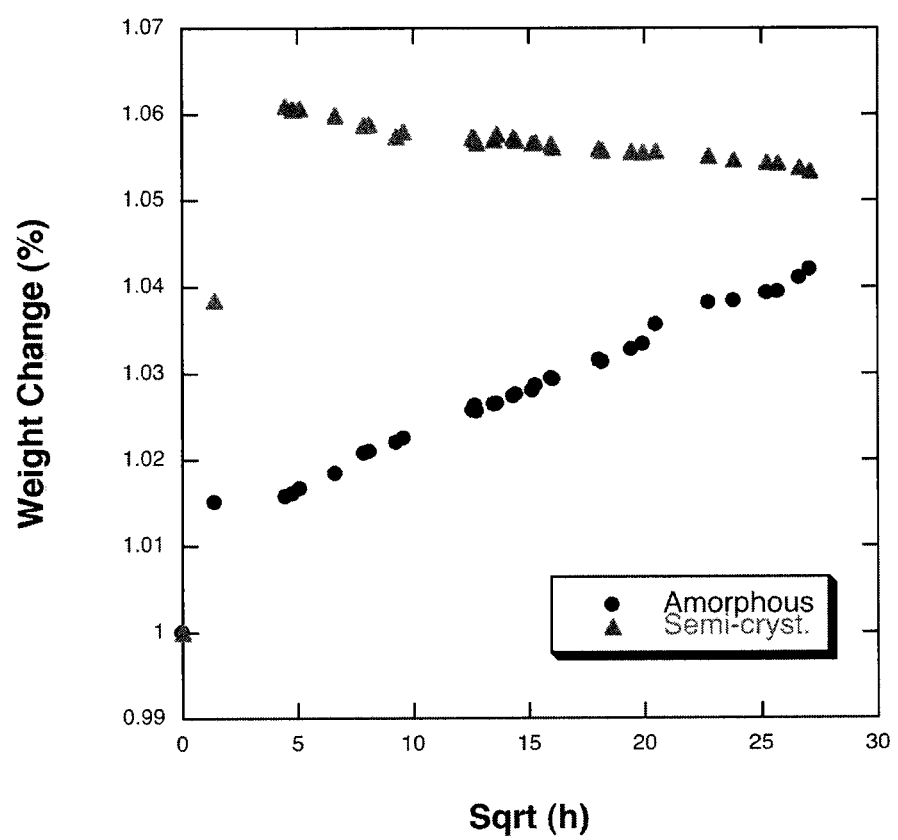
FIG. 4 shows the average sorption uptake value, weight change in %, as a function of the square root of time $(h)^{1/2}$ from the amorphous and semi-crystalline PLLA samples soaked in methanol.

FIG. 4 shows methanol sorption curves of amorphous PLLA samples. The curve has a two-stage characteristic diffusion with different sorption kinetics. It has a fast initial methanol uptake, of 1.5%, within the first two hours of methanol soaking, followed by a slow and linear penetrant sorption of methanol that did not reach saturation within 4 or 5 weeks. The slow methanol uptake of amorphous PLLA samples is somewhat unexpected compared to the methanol sorption of semi-crystalline PLLA samples, also shown in FIG. 4. The curve has two-stage characteristic behavior due to competing mechanisms between solvent induced crystallization and sorption uptake.

The semi-crystalline samples have a fast linear initial uptake that reaches saturation, at or about 6%, within at, or about 25 h. The diffusion is similar to the Fickian (case I) diffusion. However, the sorption does not reach constant uptake but rather decreases, almost down to 5%, with additional soaking time.

Possible explanations for the decrease in weight change of methanol sorption can be that low molecular weight chains inside the bulk material are slowly being filtered out from the material. Another hypothesis is that the decrease in weight change is due to solvent induced crystallization [S Mitsuhiro, T Naozumi, I Yusuke: Polymer (2007), 48, (9), 2768-2777], which was tested with DSC studies discussed herein. The latter hypothesis of induced crystallization can also be the reason to the slow uptake of methanol in the amorphous PLLA samples.

Furthermore, since the methanol sorption of amorphous PLLA is slow already after 2 h of soaking, it also means that induced crystallization occurs very fast. This indicates that methanol sorption of the amorphous PLLA samples has two mechanisms that counteract each other. The methanol sorption in semi-crystalline PLLA samples is fast. In addition, it is believed that lower methanol uptake is obtained from the amorphous PLLA samples than the semi-crystalline samples as a consequence to the induced crystallization.

Figure 5:
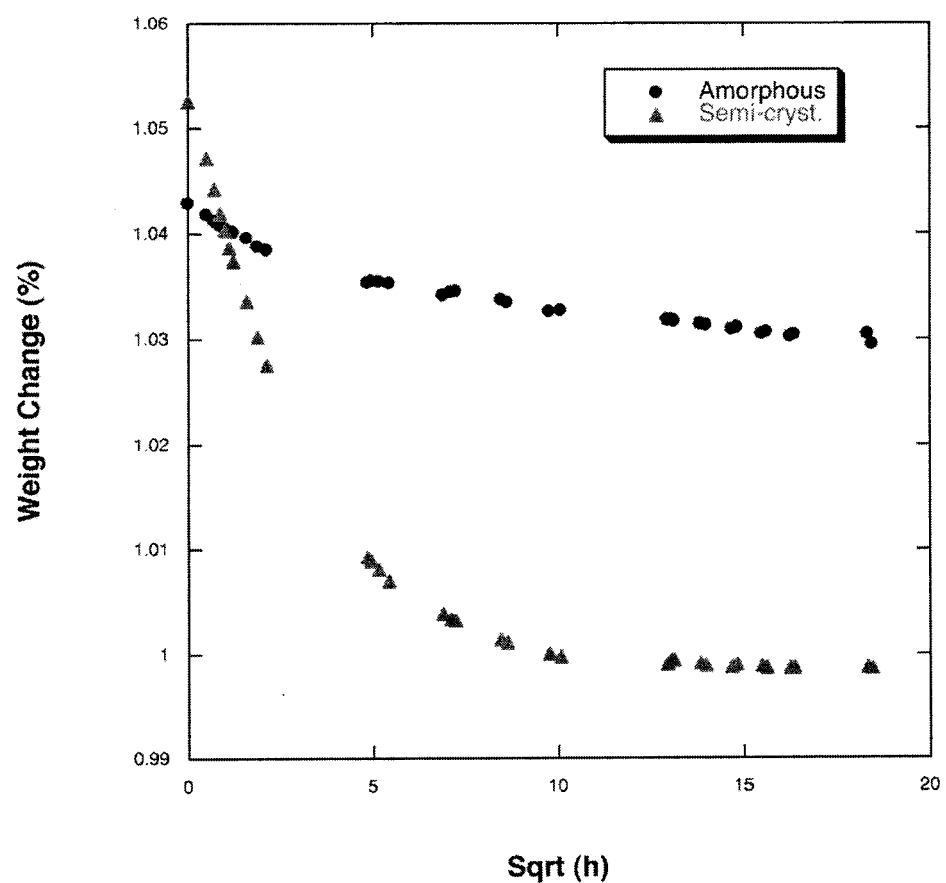
FIG. 5 shows the average desorption value, weight change in %, as a function of the square root of time $(h)^{1/2}$ from the amorphous and semi-crystalline PLLA samples soaked in methanol.

FIG. 5 shows the desorption of the methanol soaked PLLA samples. The amorphous PLLA samples did not reach the initial weight, prior to sorption experiments, within the time-frame of the desorption experiments. The desorption curve exhibits variation in desorption kinetics, being slightly steeper the first 25 hours and slowly flattening out during rest of the desorption experiment. Desorption of the semi-crystalline PLLA samples appears to correlate with the sorption of methanol uptake, a fast uptake also results in a fast desorption. Furthermore, desorption of the semi-crystalline PLLA samples soaked in methanol did reach a weight below the initial weight of the samples prior to the sorption experiments. This supports the theory that low molecular weight chains inside the bulk material were slowly being filtered out from the material, as described above.

Ethanol Sorption and Kinetics

Figure 6:
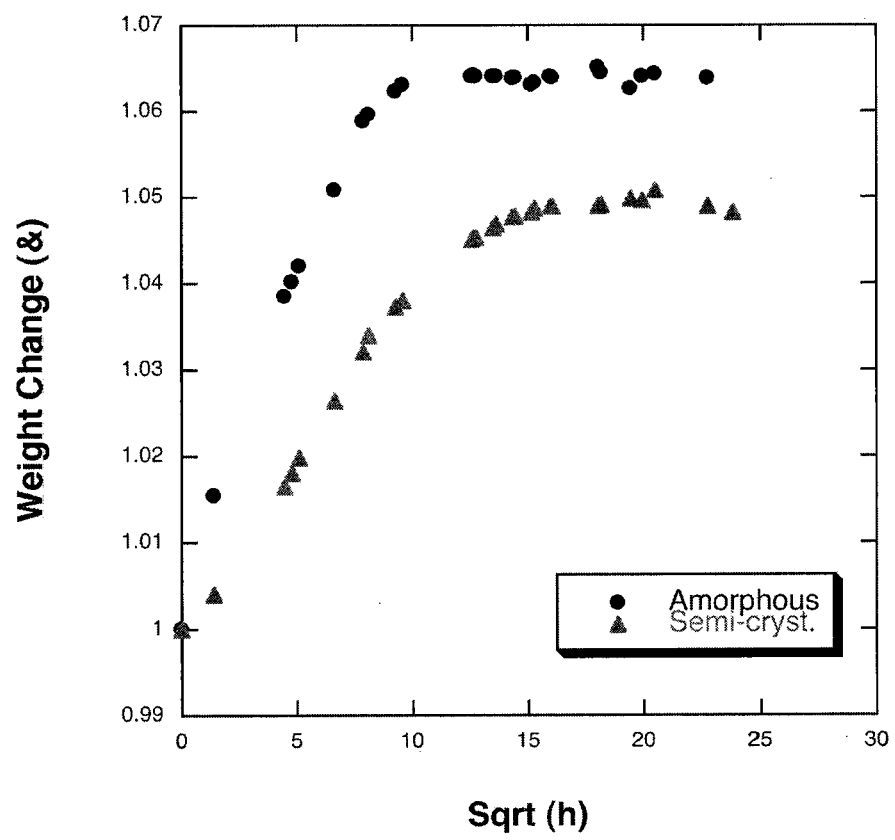
FIG. 6 shows the average sorption uptake value, weight change in %, as a function of the square root of time $(h)^{1/2}$ from the amorphous and semi-crystalline PLLA samples soaked in ethanol.

FIG. 6 shows the ethanol sorption of amorphous and semi-crystalline PLLA samples. Ethanol sorption of the amorphous PLLA samples has a linear uptake in the beginning of the curve, and when sorption saturation is reached at about 6% in about 4 days, the curve levels off and a constant penetrant uptake is obtained; showing that ethanol sorption of amorphous PLLA samples also obeys Fickian (case I) diffusion behavior. FIG. 6 also shows that the ethanol uptake of 6% which is much higher than the water sorption of the amorphous PLLA.

The sorption curve of semi-crystalline PLLA samples soaked in ethanol has a slight S-shaped form indicating a non-Fickian or anomalous diffusion behavior. The saturation uptake of 5% was reaches in about 8 days. This behavior tends to occur when the diffusion and relaxation rates are comparable, and it is associated with the restricted rates at which the polymer structure may change in response to the sorption of penetrant molecules. In addition, the ethanol sorption of semi-crystalline samples also has a higher penetrant uptake, 5%, than semi-crystalline PLLA samples soaked in water.

Ethanol uptake of the amorphous PLLA samples was also higher than the semi-crystalline samples, however, the difference was not as high as 40% more uptake for the amorphous samples. The difference between amorphous PLLA and semi-crystalline PLLA is less than 40% after a certain time of soaking, which results in a lower difference in uptake between the PLLA samples. A hypothesis for the lower difference of ethanol uptake between the amorphous PLLA compared to the semi-crystalline PLLA is also that it is due to solvent induced crystallization, which was tested with DSC and discussed herein.

Furthermore, soaking time to reach sorption saturation was much longer for ethanol sorption than water sorption. The amorphous PLLA samples took about 4 days to reach saturation of 6%, while it took about a week for the semi-crystalline samples to reach saturation. A possible explanation for the longer sorption saturation time is that the amount of ethanol sorption is much higher than the water sorption. It is believed that the difference in uptake is due to the different hydrophilicity between water and ethanol or affinity and solubility with PLLA, since both water and ethanol are hydrophilic.

Figure 8:
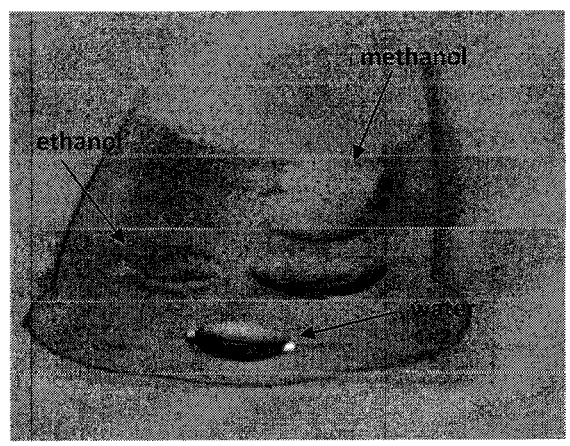
FIG. 8 depicts an image of water-, ethanol-, and methanol droplet on semi-crystalline samples shows the affinity between the solvents the material.

FIG. 8 shows an affinity test of penetrant and semi-crystalline PLLA. The image shows how the water forms a droplet on the material indicating hydrophobic characteristic of the PLLA. However, ethanol and methanol do not form a droplet showing that those two solvents have a high affinity with the material. Due to the high affinity, the ethanol and methanol are able to penetrate into the material thus leading to rather high sorption of approximately 6%. Water on the other hand does not seem to be absorbed or penetrate the material, thus leading to the low and fast uptake of water soaked samples.

Figure 7:
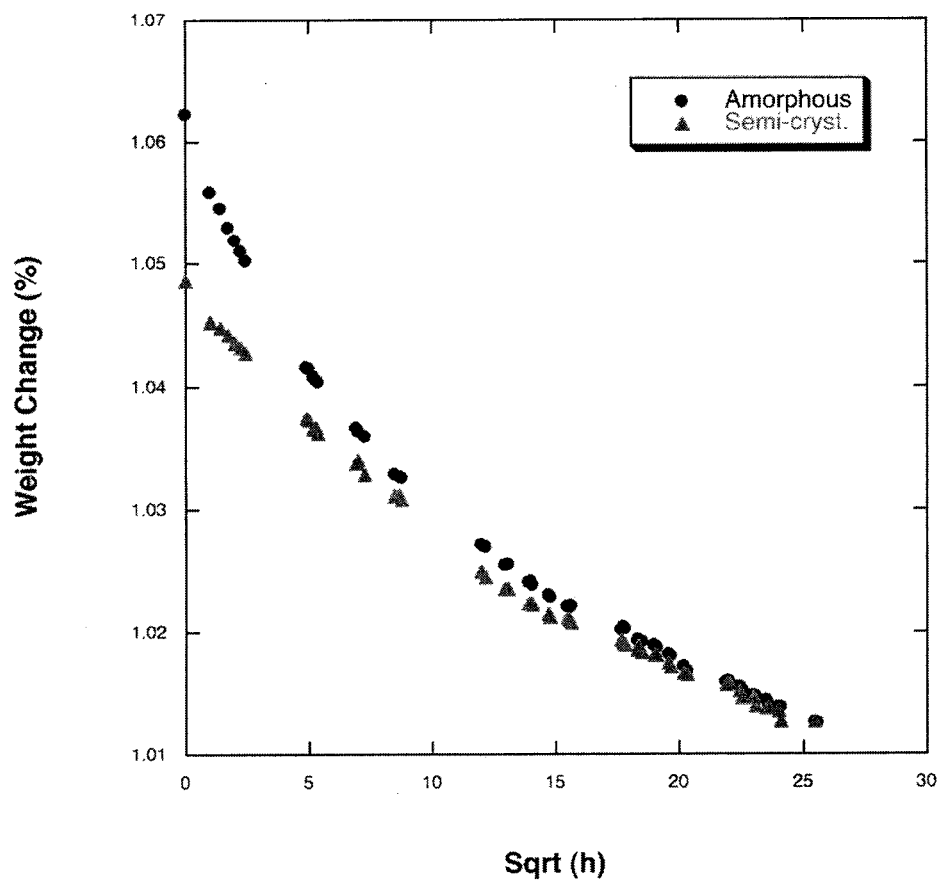
FIG. 7 shows the average desorption value, weight change in %, as a function of the square root of time $(h)^{1/2}$ from the amorphous and semi-crystalline PLLA samples soaked in Ethanol.

FIG. 7 shows desorption of the ethanol soaked PLLA samples. As can be seen on the desorption curves, none of the amorphous or semi-crystalline PLLA samples reached the initial weight within the time frame of the desorption experiments. The desorption of ethanol soaked samples did not appear to correlate with the sorption uptake as was shown in the case of water, desorption of ethanol seemed to be slower than the sorption uptake. A possible reason is the stronger affinity between ethanol and PLLA, which may require stronger desorption mechanism than the way the experiments were conducted. Conducting desorption in vacuum may have dried out the samples faster and completely by reaching the initial weight.

Furthermore, another possible explanation to the slow desorption lies within the crystal structure of the PLLA. Depending on the crystallization conditions, it is possible that a polymorphic crystal structure has been obtained, containing α and α' crystals. It has been reported that the α' is less stable and is characterized by a slightly larger lattice dimension and looser PLLA chain arrangements. [M. L Di Lorenzo, et al., Crystal polymorphism of poly(L-lactic acid) and it's influence on thermal properties, Thermochim. Acta (2011), doi: 0.1016/j.tca.2010.12.027] It may be possible that the larger and looser α' crystal structure encapsulates the methanol and traps the molecules inside the lattice, thus resulting in slower desorption of ethanol.

Thermal Analyses
DSC Characterization of Amorphous PLLA Samples Soaked in Water, Ethanol and Methanol The change of fictive temperature of all the wet PLLA samples is presented in Table 2, while fictive temperatures of the dried samples are presented in Table 3.

TABLE 2

Calculated fictive temperature of amorphous PLLA and semi-crystalline PLLA samples at wet state after soaking.

| | \multicolumn{7}{c}{Soaking time:} | | | | | | |
|---|---|---|---|---|---|---|
| | No soaking | 1 h | 5 h | 25 h | 72 h | 1 week | 4 weeks |
| Amorphous PLLA | | | | | | | |
| Water samples | 58.0 | 56.9 | 53.4 | 50.1 | 45.7 | 44.6 | 41.7 |
| Ethanol Samples | 58.0 | 54.6 | 53.8 | 53.4 | 49.8 | 46.0 | 40.8 |
| Methanol Samples | 58.0 | 54.7 | 45.8 | 33.0 | 34.7 | 34.1 | 34.8 |

TABLE 2-continued

Calculated fictive temperature of amorphous PLLA and semi-crystalline PLLA samples at wet state after soaking.

| | No soaking | 1 h | 5 h | 25 h | 72 h | 1 week | 4 weeks |
|---|---|---|---|---|---|---|---|
| Semi-cryst. PLLA | | | | | | | |
| Water samples | 75.6 | 70.8 | 69.1 | 69.5 | 72.5 | 71.3 | 66.3 |
| Ethanol Samples | 75.6 | 69.2 | 66.2 | 51.7 | 48.5 | 43.3 | 45.7 |
| Methanol Samples | 75.6 | 67.5 | 63.99 | 47.8 | 37.9 | 36.9 | 37.9 |

TABLE 3

Calculated fictive temperature of dried amorphous PLLA and semi-crystalline PLLA samples.

| | No soaking | 1 h | 5 h | 25 h | 72 h | 1 week | 4 weeks |
|---|---|---|---|---|---|---|---|
| Amorphous PLLA | | | | | | | |
| Water samples | 58.0 | 55.20 | 58.13 | 52.13 | 51.13 | 51.12 | 49.39 |
| Ethanol Samples | 58.0 | 55.84 | 55.76 | 55.26 | 52.42 | 52.28 | 47.23 |
| Methanol Samples | 58.0 | 54.51 | 50.08 | 47.20 | 54.04 | 59.36 | 58.10 |
| Semi-cryst. PLLA | | | | | | | |
| Water samples | 75.6 | 68.97 | 69.19 | 71.30 | 69.59 | 72.03 | 69.19 |
| Ethanol Samples | 75.6 | 71.11 | 68.34 | 64.88 | 67.13 | 62.38 | 62.40 |
| Methanol Samples | 75.6 | 69.56 | 69.04 | 64.38 | 72.45 | 72.64 | 73.77 |

Figure 9:
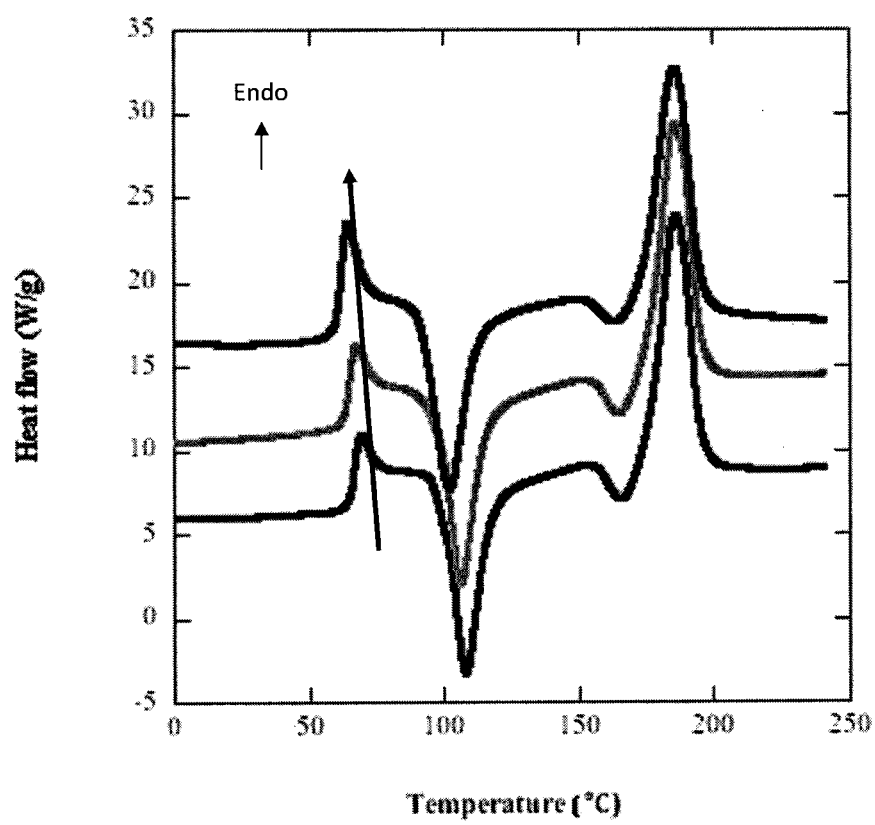
FIG. 9 shows the DSC thermograms of water soaked amorphous PLLA samples.

FIG. 9 shows DSC thermograms of water soaked amorphous PLLA samples. The reference sample in the bottom, followed by samples that have been soaked 1 day (middle), and 4 weeks (top). FIG. 9 shows that the hysteresis peak is shifted to the left with increased soaking time, as shown with the arrow, starting at 68.5° C. and ending at 63.5° C. after 4 weeks soaking. A consequence of this shift is a depressed fictive temperature which changes the glassy structure of the polymer. Furthermore, a shift of the cold crystallization peak also occurs, decreasing from 106° C. down to 100° C. after 4 weeks of soaking. The fictive temperature of wet state, water soaked amorphous PLLA samples, was lower than the dried samples that been soaked more than 25 hours. These results indicate that water sorption does lower the $T_f$ of amorphous PLLA. Furthermore, by comparing the $T_f$ values obtained by aging the samples at 40° C. [16] in dried environment, presented in table 3, the results also indicate that PLLA ages faster in wet environment than in dry environment.

Figure 10:
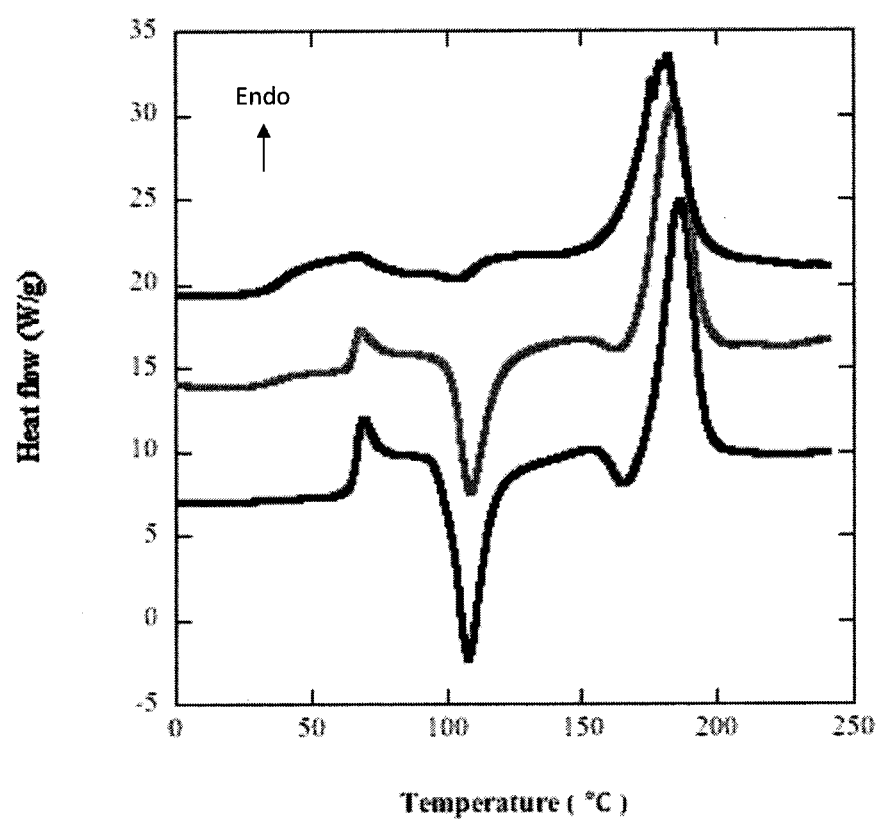
FIG. 10 shows the DSC thermograms of ethanol soaked amorphous PLLA samples.

FIG. 10 shows DSC thermograms of ethanol soaked amorphous PLLA samples. The reference sample is at the bottom, followed by samples that have been soaked 3 days (middle), and 4 weeks (top), respectively. The thermograms show a major difference in the ethanol soaked samples compared to the water soaked samples. A transition is shown to develop in the region around 37° C., indicating a double Tg. After 4 weeks of soaking the double Tg has disappeared into one Tg, resulting in a wide range of the Tg. The hysteresis peak is also shifted to left, as the water soaked samples, and simultaneously the cold crystallization peak is diminished with soaking time and is almost erased after 4 weeks of soaking, as shown by the top-most curve. This indicates that the degree of crystallinity in the samples increases with soaking time in ethanol since; the degree of crystallinity in the samples is calculated by subtracting the cold crystallization peak with the crystallization melting peak.

For non-treated samples, references, the degree of crystallinity is 1-2%. After 4 weeks of soaking in ethanol, the degree of crystallinity is 58%. Some increase of heat flow in the thermograms is due to evaporation heat of the ethanol penetrant, however, the ethanol sorption curve of amorphous PLLA samples in FIG. 6, which showed that sorption saturation, is reached within 1 week of sorption in ethanol. This indicates no increase of ethanol uptake occurs when saturation is reached for the ethanol soaked samples, however, the thermograms in FIG. 10 showed a gradual decrease in cold crystallization peak even after 1 week, meaning that an increased and induced crystallization is obtained due to ethanol sorption of amorphous PLLA samples. $T_f$ of the ethanol soaked samples is lower for all the wet amorphous samples compared to dried samples, which shows the plasticizing effect of ethanol on PLLA.

Figure 11:
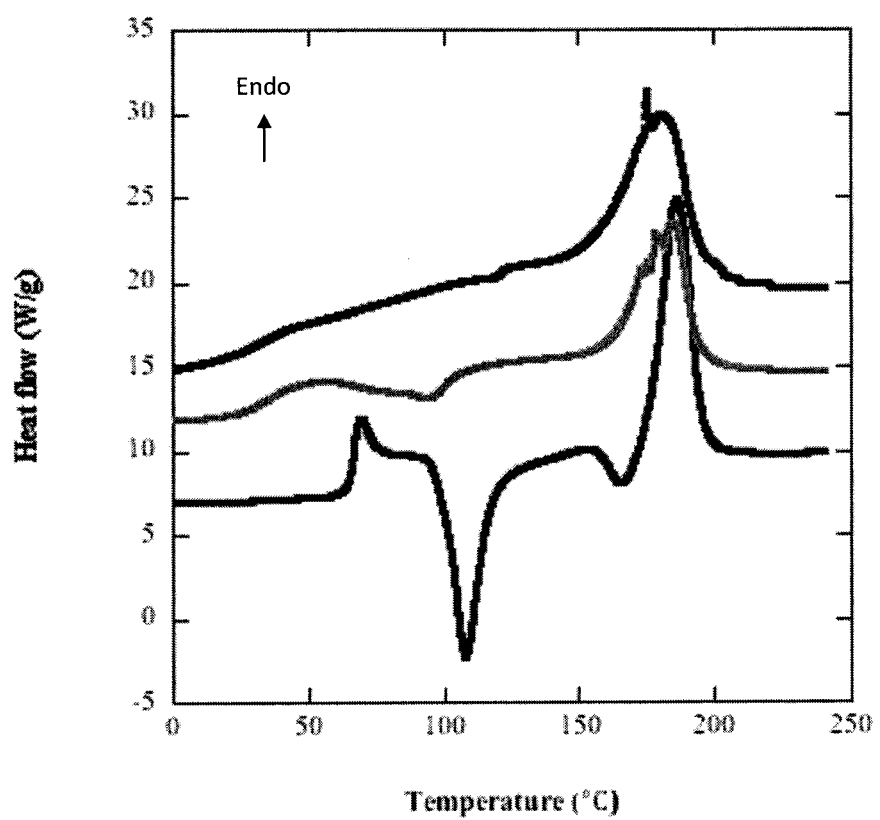
FIG. 11 shows the DSC thermograms of methanol soaked amorphous PLLA samples.

FIG. 11 shows the DSC thermograms of methanol soaked amorphous PLLA samples. The curve of the reference sample is at the bottom, followed by samples that have been soaked 1 day (middle), and 4 weeks (top) respectively. The characteristic thermograms of methanol soaked samples are even more different compared to the thermograms on FIGS. 9 and 10. It can be seen on FIG. 11 that after 1 day of soaking the thermogram of methanol soaked samples, middle curve, show similar character to the 4 weeks of soaking in ethanol in FIG. 10 (topmost curve). The degree of crystallinity of the methanol soaked sample is 62%, which is comparable to the 58% crystallinity, obtained from 4 weeks of ethanol soaked samples.

Furthermore, the amorphous PLLA samples do not show any cold crystallization at all after 3 days of soaking, and the trend remains even after 4 weeks of soaking time. In addition, due to the erased cold crystallization peak, the fictive temperature is rapidly depressed from 58° C. down to 34° C. within 1-2 days of soaking in methanol at 37° C., as shown in Table 2.

Figure 12:
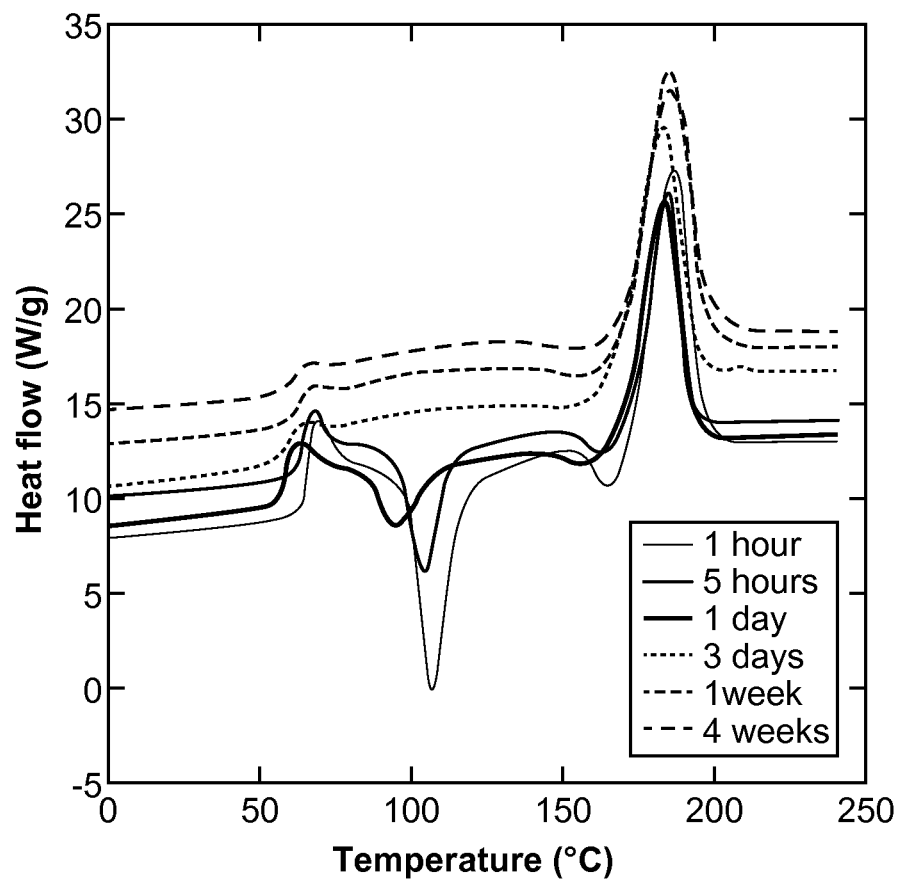
FIG. 12 shows DSC thermograms of the dried methanol soaked amorphous PLLA samples.

FIG. 12 shows DSC thermograms of the dried methanol soaked amorphous PLLA samples. The dried methanol soaked samples of amorphous PLLA characterized with DSC showed that after 25 hours of soaking the cold crystallization peak has disappeared when the samples have been dried out. This indicates that an irreversible change in morphology has occurred, transitioning the samples from amorphous to a semi-crystalline structure. Without the cold crystallization peak of amorphous PLLA the thermograms look somewhat similar to the thermograms of semi-crystalline PLLA, shown in FIG. 13.

Figure 13:
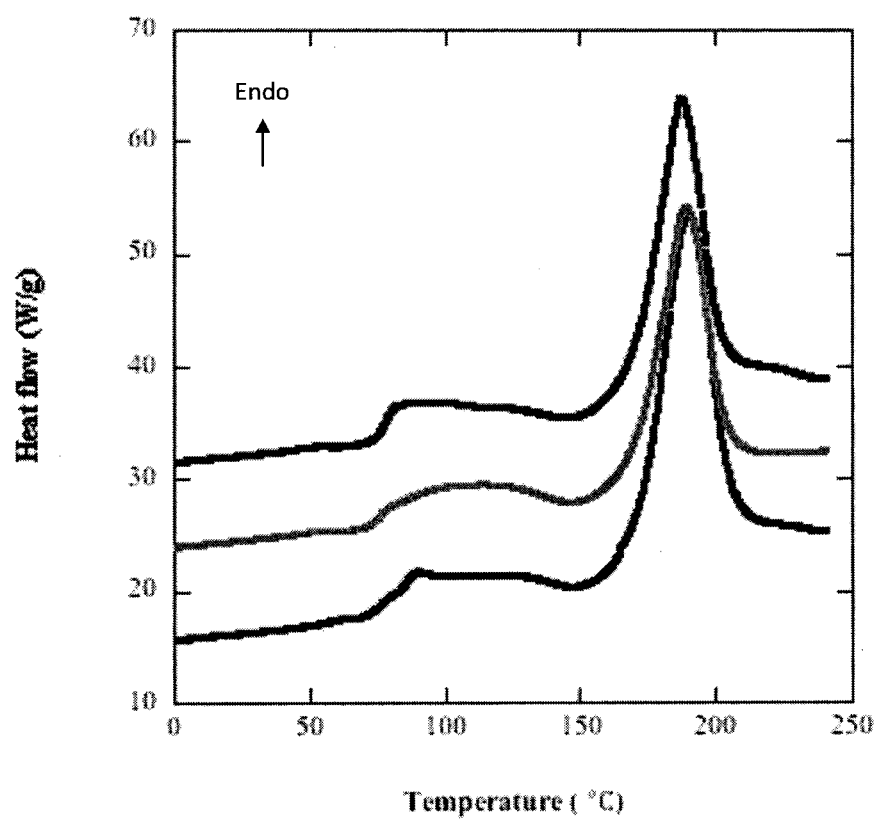
FIG. 13 shows the DSC thermograms of water soaked semi-crystalline PLLA samples.

However, the most remarkable difference between methanol induced crystallization shown in FIG. 12, and the semi-crystalline PLLA DSC thermograms in FIG. 13, is that there is two semi-crystalline PLLA structures with different $T_g$. The $T_g$ from methanol induced crystallization of the isotropic amorphous PLLA samples are approximately 58° C., the same as the initial fictive temperature. While the highly oriented semi-crystalline PLLA samples have a $T_g$ of 75° C. The difference in chain orientation obtained by the two processing methods shows up as different Tg's and means it is possible to obtain semi-crystalline PLLA with the same $T_g$ as amorphous PLLA by methanol induced crystallization. This more isotropic PLLA should have more stable shelf-life properties and most likely better fracture fatigue properties.

Figure 14:
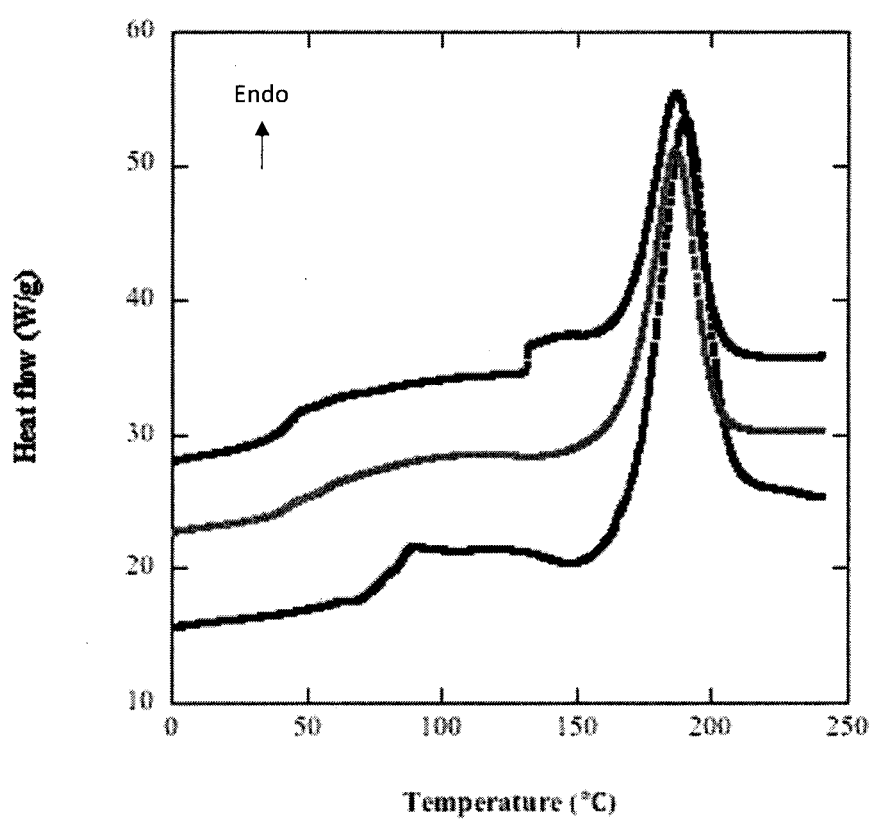
FIG. 14 shows the DSC thermograms of ethanol soaked semi-crystalline PLLA samples.
Figure 15:
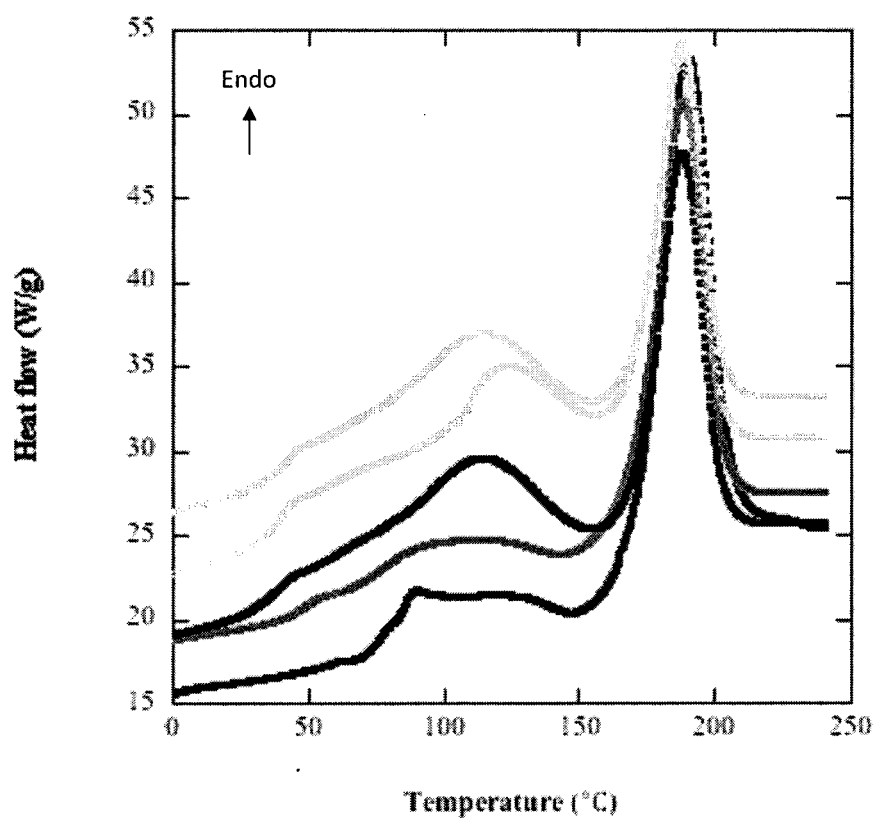
FIG. 15 shows the DSC thermograms of methanol soaked semi-crystalline PLLA samples.

DSC Characterization of Semi-Crystalline PLLA Samples Soaked in Water, Ethanol and Methanol FIGS. 13, 14, and 15 show DSC thermograms of water-, ethanol-, and methanol-soaked semi-crystalline PLLA samples, respectively. In FIGS. 13 and 14, the thermograms show the reference sample in the bottom, followed by average value of samples that have been soaked 3 days (middle) and 4 weeks (top), respectively. In FIG. 15, the reference sample in the bottom, followed by samples that have been soaked 1 day, 3 days, 1 week, and 4 weeks. The change of fictive temperature from the semi-crystalline PLLA samples is presented in Table 2.

The water soaked samples of semi-crystalline PLLA did not show any change in degree of crystallinity. However, a small change of the fictive temperature was measured, presented in Table 2, which shows that a fast initial drop of fictive temperature occur after one hour of soaking; depressing the fictive temperature from 75.6° C. down to 70.8° C. The fictive temperature then remains around 69-71° C., independent of soaking time. However, after 4 weeks of soaking the fictive temperature is depressed further down to 66° C.

The change of fictive temperature for semi-crystalline PLLA samples soaked in ethanol and methanol is also presented in Table 2. Thermograms for the ethanol (FIG. 14) and methanol (FIG. 15) soaked samples showed different characteristic behavior compared to the water soaked samples, FIG. 13, in which all the thermogram curves look similar to each other. The fictive temperature in both ethanol and methanol soaked samples were much more depressed than the water soaked samples, having a fictive temperature around 45° C. and 37° C., respectively, after 4 weeks of soaking time.

Furthermore, the thermograms of the semi-crystalline samples soaked in ethanol and methanol also indicates an induced crystallization, having an additional melting peak that increases with soaking time. This is more distinguishable for the methanol soaked samples, FIG. 15. As mentioned before, there is an increase in heat flow contributed by the heat of evaporation of the ethanol and methanol penetrants. The relative contribution of the increase in heat flow from the heat of evaporation and melting of crystals is not shown by the data. However, by looking at the sorption curve for semi-crystalline PLLA samples soaked in methanol, FIG. 5, it can be seen that saturation is reach within 25 h indicating that no increase of methanol uptake occurs. Instead a slight decrease of the methanol sorption uptake can be seen. It is believed that this due to induced crystallization, which is shown by the DSC thermograms. Since there is no additional uptake of methanol after 1 day of soaking, this indicates that there should not be any more contribution from heat of evaporation for samples soaked 3 days and longer. However, it is clearly seen on thermograms for the methanol soaked samples, FIG. 15, that the heat flow and melting peak increase with soaking time, indicating that induced crystallization does occur for methanol soaked samples. Although the data for induced crystallization is not as evident for ethanol soaked samples, there are reasons to believe that it does occur, since it occurs for amorphous PLLA soaked in ethanol.

DSC characterization of dried semi-crystalline samples soaked in water, ethanol, methanol did not show any major change in crystallinity. However the change in $T_f$ of the dried samples, presented in Table 3, shows that the $T_f$ of the water soaked samples rapidly decreases to 69° C., already after 1 hour of soaking, and is kept there ±1° C. independent of the soaking time. Dried ethanol soaked samples do show a steady decrease of $T_f$ being kept around 62° C. after one week of ethanol soaking.

However, looking back at FIG. 7, the desorption curve of ethanol soaked samples, it showed the difficulty for ethanol to desorb. Considering that the wet samples had a much lower $T_f$ it is possible that the samples were not completely dry at the moment of DSC characterization. The dried methanol soaked samples showed a u-shaped change of $T_f$, indicating that it decreased the first 25 hours of soaking from 75.6° C. to 64.4° C. and increased to 72° C. after 72 hours of soaking. It remained at 72±1° C. even after 4 weeks of soaking, indicating a decrease in $T_f$ of only 2° C. after 4 weeks of aging.

Referring to FIG. 12, the amorphous PLLA undergoes an irreversible change. The same change may occur in the amorphous phase on the semi-crystalline samples, which results in a polymorphic crystal structure and consequently results in a very low change of $T_f$ at dry state of the methanol soaked samples, compared to water and ethanol soaking.

X-Ray Measurements

Figure 16:
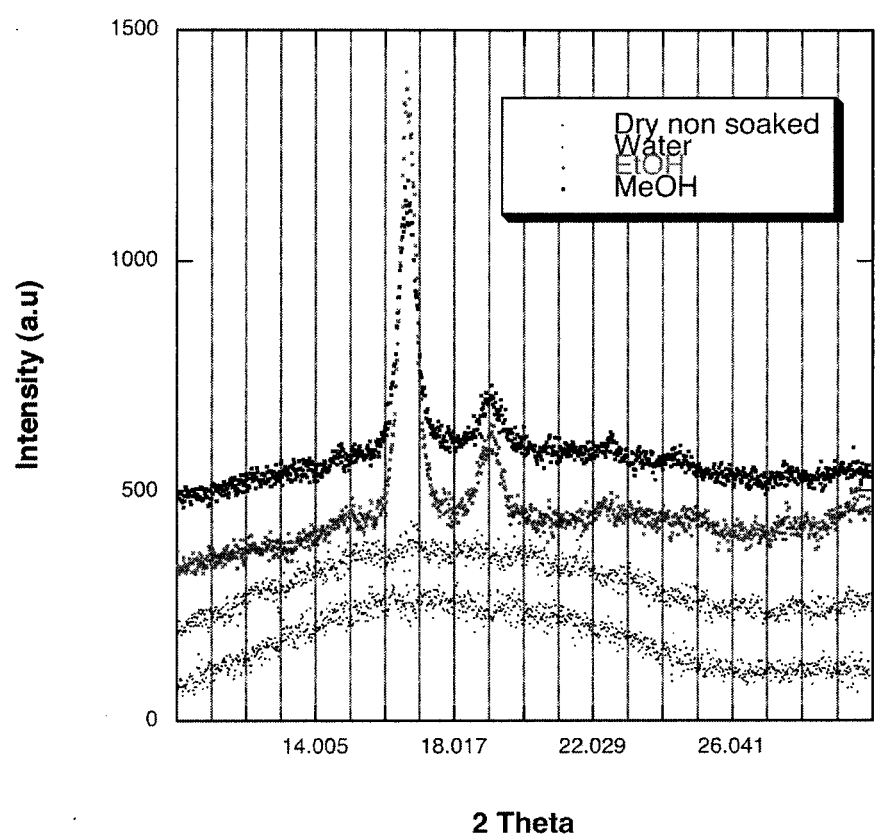
FIG. 16 shows the WAXD pattern of dry amorphous sample without soaking at the bottom of the FIG. followed by water-, ethanol-, and methanol soaked amorphous PLLA samples.
Figure 17:
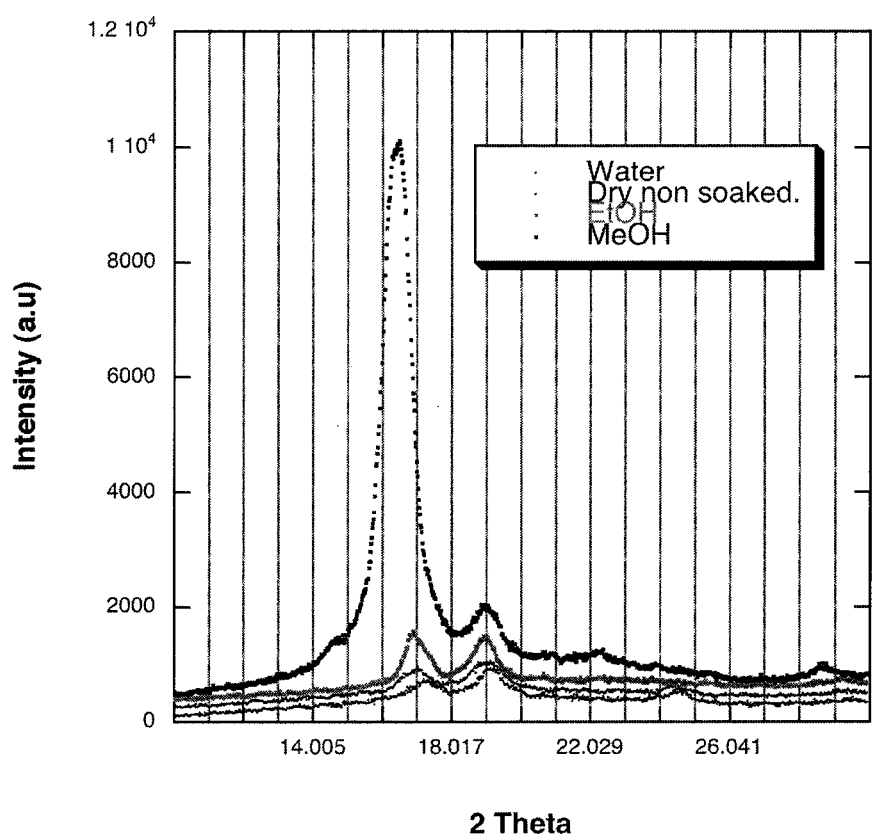
FIG. 17 shows the WAXD pattern of dry semi-crystalline sample without soaking at the bottom of the FIG. followed by water-, ethanol-, and methanol soaked PLLA samples.

WAXD patterns of the amorphous and semi-crystalline PLLA samples are shown in FIGS. 16 and 17, respectively. FIG. 16 shows the WAXD pattern of the dry amorphous sample without soaking at the bottom of the figure. The WAXD pattern of samples soaked in water is second from the bottom. These two samples show an amorphous halo, indicating there is no change in crystallinity when soaking the samples in water for 4 weeks.

The WAXD patterns of the ethanol and methanol soaked samples are second from the top and the top-most, respectively on the figure. For both of these patterns, two peaks at approximately 16.7° and 19.1°, have appeared after soaking the samples for 4 weeks. The peaks at those 2θ values corresponds to reflection of (2 0 0)/(1 1 0) and (2 0 3) planes in an α-crystallized orthorhombic unit cell [17].

FIG. 17 shows the WAXD pattern of dry semi-crystalline sample without soaking at the bottom of the figure with peaks at approximately 17.3°, 19.2° and 24.3°. A shift of 2θ values of crystals is possible and depends on crystallization temperature, $T_c$. The first two peaks indicates α-crystals with a shift on the (2 0 0)/(1 1 0) planes from 16.7° to 17.3° and from 19.1° to 19.2° of the (2 0 3) plane. The additional peak, compared to FIG. 16, at 24.3° indicates a polymorphic structure where α- and α'-crystals coexist [15]. The same kind of peaks is also shown in FIG. 17 on the water soaked samples, second from the bottom, as well as the two other peaks around 17° and 19°, indicating that no change in crystallinity has occurred from the water treatment.

For the ethanol soaked samples, the second from the top in FIG. 17, the WAXD patterns show higher intensity of the peaks around 17° α- and α'-crystals and 19° than the non- and water soaked samples. The higher intensity indicates an increase in the degree of crystallinity of the sample. Furthermore, whether the peak around 24.3° has disappeared or diminished. Its disappearance indicates that the ethanol soaking may have transitioned the polymorphic crystal structure of α- and α'-crystals to pure α-crystalline structure. However, it is believed that that such transition is unlikely to occur only due to ethanol soaking and that such a difference may require thermal treatment to obtain such a transition. Furthermore, the slow desorption of ethanol shows that some kind of entrapment of ethanol molecules does occur.

The WAXD patterns of the methanol soaked samples, the top-most curve in FIG. 17, shows an extremely high increase of the intensity at 16.5°, which is a slight shift of the peak compared to the non-, water-, and ethanol soaked samples. There are also additional peaks appearing at 14.6°, 22.3° and 28.7° which corresponds to reflection of (0 1 0), (0 1 5) and (0 1 8) planes respectively. The peaks corresponds to crystallization of PLLA between 105° C.≤$T_c$≤125° C., which also means that methanol soaking results in a polymorphic structure where α- and α'-crystals coexist [15].

Tensile Testing and Change of Mechanical Properties

The change of mechanical properties of semi-crystalline PLLA samples due to soaking time and uptake of penetrant are presented in Table 4. Soaking time was 2 min, 70 min and 8 days in water, ethanol and methanol at 37° C., as well as samples dried for 4 days after 70 min and 8 days of soaking of ethanol and methanol soaked samples.

TABLE 4

Mechanical testing data of semi-crystalline PLLA E-modulus in units of GPa.

| Solvent | Reference | 2 min | 70 min | Dried | 8 days | Dried |
|---|---|---|---|---|---|---|
| Water | | | | | | |
| E modulus | 1.81 | 1.84 | 1.72 | 1.86 | 1.61 | No data |
| Elongation % | 57 | 31 | 33 | 23 | 19 | No data |
| Ethanol | | | | | | |
| E modulus | 1.81 | 1.73 | 1.66 | 1.83 | 1.28 | 1.64 |
| Elongation % | 57 | 45 | 64 | 19 | 97 | 117 |
| Methanol | | | | | | |
| E modulus | 1..81 | 1.76 | 1.42 | 1.92 | 1.13 | 1.52 |
| Elongation % | 57 | 56 | 101 | 18 | 180 | 33 |

The water soaked samples showed a slight change of mechanical properties with a decrease in E-modulus from 1.81-1.61 GPa after 8 days of soaking, and a lower strain at break resulting in a less flexible and stiffer material.

The ethanol soaked samples showed a decrease in E-modulus from 1.81 to 1.71 GPa (about a 6% drop) and 1.81 to 1.28 GPa (about a 30% drop) after 8 days of soaking, however, the strain at break increased from 45% up to 97% (about 116% increase) indicating that a softer and more flexible material is obtained, as a result of ethanol soaking. This indicates that ethanol soaking has a plasticizing effect on the semi-crystalline PLLA samples.

Methanol soaked samples showed similar results to the ethanol soaked samples; however, the plasticizing effect was enhanced. Additionally, soaking in methanol appears to be more efficient due to similar properties that can be obtained from shorter soaking time; 8 days ethanol soaking compared with 70 min methanol soaking. The E-modulus decreased from 1.81 to 1.42 GPa in 70 min (about 21% drop) and to 1.13 GPa (about 38% drop) in 8 days of soaking. The elongation increased from 57 to 101% (about 77% increase) in 70 min and to 180 in 8 days (about a 216% increase). This shorter time is probably due to faster uptake of methanol than ethanol in the material.

However, both ethanol and methanol sorption in semi-crystalline PLLA reached saturation after 8 days of soaking, as shown in FIGS. 7 and 5. Yet methanol soaked samples show a much more flexible property than the ethanol soaked samples. This is further evidence of methanol as a much more efficient plasticizer than ethanol for semi-crystalline PLLA.

Also shown in Table 4, 4 days of drying after the soaking at 70 min, the E-modulus increased for all samples, and was even higher than the initial E-modulus before soaking. Furthermore, all the samples had also become stiffer. 4 days of drying after 8 days of soaking the ethanol samples had an increased E-modulus compared to the wet state. However, the strain at break increased which is not expected, since it is expected to become stiffer in dry state than wet state. Considering that 4 days of drying is not sufficient to dry the ethanol soaked samples, this is still surprising results. 4 days of drying of the methanol soaked samples showed that the samples had a higher E-modulus at dry state than wet state and had become stiffer.

The plasticizing effect of ethanol and methanol soaked samples shows that they are efficient as solvents for physical modification of semi-crystalline PLLA. The reason that water does not show the same plasticizing effect is probably due to insufficient penetration into the material. The water only adsorbs to the surface and is not able to penetrate into the bulk. Ethanol and methanol, on the other hand, are able to penetrate into the bulk material and as a result they work well as plasticizers.

Summary of Results

Water sorption of amorphous and semi-crystalline PLLA samples obeyed Fickian diffusion, with an uptake of 0.06 and 0.1%, respectively, saturation was reached within 25 h in both cases. Water sorption also depressed the amorphous and semi-crystalline PLLA. However, no change in crystallinity was obtained from water soaking.

Ethanol sorption of amorphous PLLA samples obeyed Fickian diffusion. DSC of ethanol soaked samples also showed induced crystallization as did methanol soaked samples. The semi-crystalline samples showed anomalous non-Fickian diffusion behavior. The ethanol uptake was about 6% for amorphous PLLA and the saturation time was about 4 days, while the ethanol uptake for semi-crystalline PLLA was about 5% and took about 8 days to reach saturation.

Methanol sorption of amorphous PLLA samples are similar to Fickian diffusion. However, instead of constant uptake, a decrease in weight is observed which may be due to low molecular weight fractions are leaching out or due to induced crystallinity which decreases the uptake of methanol penetrant. DSC showed that the fictive temperature was significantly and rapidly depressed down to 34° C. Furthermore, the cold crystallization peak disappeared after 1-2 days of soaking resulting in induced crystallization. Semi-crystalline samples showed two-stage diffusion due to two competing mechanism, penetrant uptake and induced crystallinity which were proved with DSC.

The penetrant uptake of ethanol and methanol was approximately 5-6% on the semi-crystalline PLLA samples which is high compared to 0.1% uptake of water. This is believed due different affinity between water, ethanol and methanol with the PLLA samples, which was shown to be much higher for ethanol and methanol. This also indicates that ethanol and methanol are efficient penetrants and plasticizers, while water is not.

The mechanical testing showed the plasticizing effect of ethanol and methanol, resulting in a much more flexible material, especially from methanol soaking. However, the E-modulus also decreased as the flexibility increased.

"Molecular weight refers to either number average molecular weight (Mn) or weight average molecular weight (Mw).

"Semi-crystalline polymer" refers to a polymer that has or can have regions of crystalline molecular structure and amorphous regions. The crystalline regions may be referred to as crystallites or spherulites which can be dispersed or embedded within amorphous regions.

Figure 18:
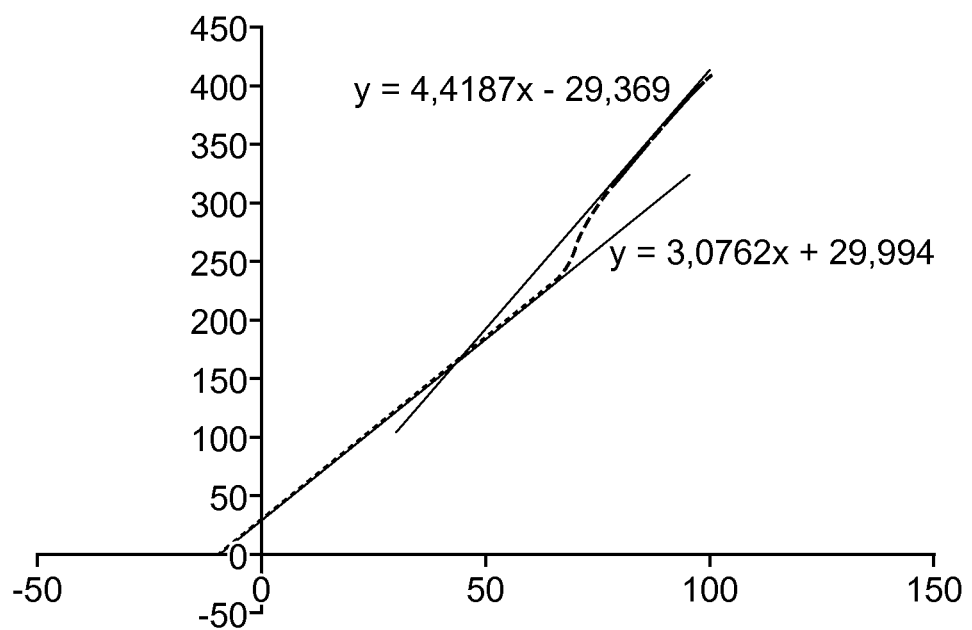
FIG. 18 depicts the intercept method of area change as a function of temperature to assess the fictive temperature.

The "fictive temperature" is defined as the temperature at which the nonequilibrium value of the macroscopic property would be the equilibrium one. A. Tool and C. G. Eichlin, J. Am. Ceram. Soc. 14, 276 (1931). $T_f$ acts as a map between a nonequilibrium glass and an equilibrium liquid. A glass at a temperature $T_1$ has the same structure as a super cooled liquid at temperature $T_f$. The fictive temperatures were calculated by using an intercept method: This method compares area change vs temperature and the trendline between these two area changes gives us the $T_f$. The two methods are illustrated on FIG. 18.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

Elongation at break of a material is the percentage increase in length that occurs before a sample made of the material breaks under tension.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" or 'stiffness' may be defined as the ratio of a component of stress or force per unit area applied to a material divided by the strain along an axis of applied force that results from the applied force. The modulus typically is the initial slope of a stress—strain curve at low strain in the linear region. For example, a material has both a tensile and a compressive modulus.

The tensile stress on a material may be increased until it reaches a "tensile strength" which refers to the maximum tensile stress which a material will withstand prior to fracture.

The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of fabricating a bioresorbable stent scaffold comprising:
   providing a tube made of a bioresorbable polymer comprising amorphous poly (L-lactide);
   exposing the tube to a fluid for a period of time to reach a % uptake of saturation, wherein the % uptake of saturation is a maximum % uptake of the fluid of the tube, wherein the fluid is methanol, wherein the fluid is absorbed into the bioresorbable polymer and increases a flexibility of the bioresorbable polymer, wherein the fluid is absorbed without dissolving the polymer;
   radially expanding the exposed tube comprising the absorbed fluid from a first diameter to a second diameter; and
   fabricating a scaffold having a pattern of interconnected struts from the radially expanded tube.

2. The method of claim 1, wherein the temperature of the exposed tube is between 20 and 30 deg C. during the radial expansion.

* * * * *